(12) United States Patent
Zeng

(10) Patent No.: US 7,262,170 B2
(45) Date of Patent: *Aug. 28, 2007

(54) PHARMACEUTICAL COMPOSITION FOR REDUCING VAGINAL ACIDITY AND TREATMENT OF VAGINITIS, AND THE USE THEREOF

(76) Inventor: Zhongming Zeng, Hanshan Hosp. Nantou, Shenzhen City, Guangdong (CN) S18052

( * ) Notice: Subject to any disclaimer, the term of this patent is extended or adjusted under 35 U.S.C. 154(b) by 476 days.

This patent is subject to a terminal disclaimer.

(21) Appl. No.: 10/798,072

(22) Filed: Mar. 11, 2004

(65) Prior Publication Data

US 2004/0229822 A1 Nov. 18, 2004

Related U.S. Application Data

(63) Continuation-in-part of application No. 09/674,062, filed as application No. PCT/CN99/00059 on Apr. 26, 1999, now Pat. No. 6,770,306.

(30) Foreign Application Priority Data

Apr. 26, 1998 (CN) ................................ 98 1 08105

(51) Int. Cl.
*A61K 38/04* (2006.01)

(52) U.S. Cl. ............................................. 514/19; 514/2

(58) Field of Classification Search ..................... None
See application file for complete search history.

(56) References Cited

U.S. PATENT DOCUMENTS 4,937,234 A    6/1990  Fahim
5,573,765 A    11/1996 Reinhard
5,858,974 A    1/1999  Little
6,770,306 B1 * 8/2004  Zeng .......................... 424/717

FOREIGN PATENT DOCUMENTS

EP          0 242 980 A2    10/1987

OTHER PUBLICATIONS

Sobel et al., American Journal of Obstetrics and Gynecology, 1995, vol. 172, pp. 1263-1268.*
Notification of Transmittal of International Prelimiary Examination Report, Form PCT IPEA/416 (Jul. 1992), dated Nov. 23, 2000, with translation.
International Preliminary Examination Report, Form PCT IPEA/409, dated Sep. 18, 2000, with translation.
Written Opinion, Form PCT/IPEA/408, dated Aug. 24, 2000, with translation.
Abstract JP880276052, Culture of *Pseudomonas* S.P. Bacteria, dated May 11, 1990.

* cited by examiner

*Primary Examiner*—Cecilia J. Tsang
*Assistant Examiner*—Roy Teller
(74) *Attorney, Agent, or Firm*—Cook, Alex, McFarron, Manzo, Cummings & Mehler Ltd.

(57) ABSTRACT

A composition is disclosed for treating a patient suffering from abnormally high acidity in the vagina, wherein the vaginal pH value is lower than 4.0. The composition consists essentially of: (a) an effective amount of the following amino acids and/or physiologically acceptable salts thereof: glutamic acid, aspartic acid, isoleucine, phenylalanine and praline; (b) an effective amount of anti-fungi drugs; and (c) a sufficient amount of pharmaceutically acceptable acid or alkali, which results in a pH of the composition from 4.0-8.0; (d). One or more pharmaceutical carriers is used for the composition. The composition is particularly useful for treating vaginitis and fungal vaginitis associated with abnormally high vaginal acidity of a pH value less than 4.0.

11 Claims, No Drawings

PHARMACEUTICAL COMPOSITION FOR REDUCING VAGINAL ACIDITY AND TREATMENT OF VAGINITIS, AND THE USE THEREOF

CROSS-REFERENCE TO RELATED APPLICATIONS

This case is a continuation-in-part of U.S. Ser. No. 09/674,062, filed on Jan. 3, 2001, now U.S. Pat. No. 6,770,306, which is incorporated herein by reference, and is the national stage application of PCT/CN99/00059, having a filing date of Apr. 26, 1999 and claiming priority to CN 98108105.3, filed on Apr. 26, 1998.

FIELD OF INVENTION

The present invention relates to a pharmaceutical composition for reducing vaginal acidity, treating abnormally high vaginal acidity, vaginitis associated with abnormally high vaginal acidity, and especially the fungal vaginitis associated with abnormally high vaginal acidity, comprising amino acids and physiologically acceptable salts of amino acids. Also, the present invention relates to the use of the said amino acids, physiologically acceptable salts of amino acids as active ingredients or auxiliaries in preparing drugs for reducing vaginal acidity, drugs for treating abnormally high vaginal acidity, vaginitis associated with high acidity, especially to their use in preparing drugs for treating fungal vaginitis associated with high vaginal acidity, and the use thereof as nutrients for vaginal mucous membranes in preparing drugs that are locally applied in the vagina. It also relates to methods for reducing vaginal acidity, treating abnormally high vaginal acidity, vaginitis associated with high vaginal acidity, and especially for treating fungal vaginitis associated with high vaginal acidity.

BACKGROUND OF THE INVENTION

Fungal vaginitis, one of the vaginal diseases with high morbidity rate, is difficult to cure radically. In U.S. more than 75% women suffer from fungal vaginitis at least once in their life. About 5% of adult women suffer from repeated vaginal fungal infection, which is difficult to cure (Jack D. Sobel, MD.Candidal Vulvovaginitis, Clinical Obstetrics and Gynecology, 1993 Vol.36 (1): 153-165). The main clinical symptoms of these vaginal diseases include vulval pruritus, vaginal pain, leukorrhagia, dyspareunia, and urodynia. Therefore, this disease is harmful to women's health status as well as to their life quality.

There are various anti-fungal drugs for treating fungal vaginitis by directly inhibiting or killing fungi. The commonly used drugs include Ketoconazole, Fluconazole, Mikostatin and Clotrimazolum. They can be administered locally in the vagina or taken orally. But most of the local vaginal anti-fungal agents contain starch and/or lactose as auxiliaries, for example, as excipient. The inventor of this application has discovered that starch, lactose or other saccharides can significantly promote acid production by vaginal bacteria, increase vaginal acidity, thus promoting fungal growth in the vagina. Therefore the starch and/or lactose contained in the pharmaceutical composition are extremely unfavorable for treating vaginal fungal infection.

Furthermore, it is not easy to achieve the satisfactory curative effect by just using these anti-fungal drugs. For example, the curative rate of anti-fungal drugs is generally 75-80% for Mikostatin and 85-90% for glyoxaline anti-fungal drugs such as Ketoconazole, Treconazole, and Fluconazole (Jack D. Sobel). Even in those patients being cured by anti-fungal drugs, the disease often relapses in following menstrual periods after stopping the treatment.

The object of the present invention is to provide a pharmaceutical composition for reducing vaginal acidity, treating abnormally high vaginal acidity, vaginitis, fungal vaginitis associated with high vaginal acidity. This invention also relates to methods for treating abnormally high vaginal acidity, vaginitis associated with high vaginal acidity, especially for treating fungal vaginitis associated with high vaginal acidity.

In order to find a new pharmaceutical composition for treating fungal vaginitis, the inventor had conducted an extensive study and eventually developed a pharmaceutical composition of this invention. By using light microscopy, the inventor examined vaginal secretions from patients who had been clinically diagnosed as fungal vulvovaginitis. However, in many cases it was very difficult to confirm the fungal infection because little fungi had been found in vaginal secretions samples. After further study, it was found out surprisingly that, the vaginal acidity in such patients was abnormally high (vaginal pH value<4.0), which could result in the damage of vaginal mucous membranes alone. Therefore, these cases were actually related to abnormal enhancement of acidity in the vagina and could be called "high acidity vaginitis". The inventor also noticed that "high acidity vaginitis" had a close relationship with repeated fungal vulvo-vaginitis. This is one of the reasons why it is difficult to cure the repeated fungal vaginitis by just using anti-fungal drugs.

The U.S. patent (U.S. Pat. No. 4,804,674) teaches a method for enhancing sperm motility, wherein amino acids and /or salts of amino acids are used to enhance sperm motility. These amino acids are mainly comprising aspartic acid, glutamic acid, arginine, histidine, asparagine, glutamine, and arginine aspartate. U.S. Pat. No. 4,804,674 does not indicate that the amino acids can reduce the acid production in the vagina. U.S. Pat. No. 4,804,674 does not mention the relationship between abnormal enhancement of vaginal acidity and fungal vaginitis, or that amino acids can be used to reverse the abnormally enhanced vaginal acidity, or to treat high acidity vaginitis and fungal vaginitis.

The U.S. patent U.S. Pat. No. 4,937,234 discloses a pharmaceutical composition of neutral salts of gluconic acid, wherein zinc gluconate is an effective bactericiocidal component. These amino acids include alanine, valine, isoleucine, proline, glycine, serine, threonine, asparagine, glutamine, lysine, arginine, histidine and mixtures thereof. They are also used as auxiliaries in the pharmaceutical composition of U.S. Pat. No. 4,937,234, wherein the main component is lysine. As shown in the examples 1 to 12 of U.S. Pat. No. 4,937,234, it is emphasized that amino acids can regulate and change the acidity of the composition to neutral, and thus reduces the stimulation of the composition and enhances the sterilization of zine agents. U.S. Pat. No. 4,937,234 particularly emphasizes that its pharmaceutical composition can be used on the neonates, old people, eyes and noses that are sensitive to acid, for treatment of diaper rash, skin dryness and vaginitis. Although different treatments and drugs are adopted for treating different types of vaginitis, U.S. Pat. No. 4,937,234 does not indicate the type of vaginitis. Furthermore, no information or data indicates or suggests whether the lysine also exerts treatment effect on vaginitis when used separately.

SUMMARY OF THE INVENTION

In order to seek a pharmaceutical composition that is effective in reducing vaginal acidity, the inventor has conducted an extensive study. Surprisingly, the inventor discovered that amino acids, salts of amino acids, oligopeptides and polypeptides could change the metabolic process of bacteria in the vagina and reduce vaginal acid production. They could be used to reduce vaginal acidity and to treat related vaginal disorders. Based on this discovery and further study, the inventor accomplished the present invention.

The invention provides a pharmaceutical composition for reducing vaginal acidity. It is characterized by containing one or more components defined as follows: amino acids, physiologically acceptable salts of amino acids, oligopeptides and polypeptides; optionally containing anti-fungal drugs; and one or more pharmaceutically acceptable carriers.

Except stated especially, amino acids mentioned in this specification include corresponding salts of amino acids. According to the invention, amino acids in the said composition are formulations or combinations of many kinds of amino acids, especially it is a composition comprising amino acids and/or the physiologically acceptable salts of amino acids thereof selected from the following groups: glutamic acid, glutamine, aspartic acid, asparagine, isoleucine, methionine, phenylalanine, tyrosine, valine, leucine, proline, threonine, cysteine, alanine, glycine, serine, lysine, arginine, tryptophane, histidine; preferably it is a composition comprising amino acids and/or the physiologically acceptable salts of amino acids thereof selected from the following group: glutamic acid, aspartic acid, isoleucine, phenylalanine, valine, leucine, proline, and threonine. More preferably it is a composition comprising amino acids and/or the physiologically acceptable salts of amino acids thereof selected from the following group: glutamic acid, aspartic acid, isoleucine, phenylalanine, and proline. The acceptable physiological salts of amino acids mentioned in the invention are sodium salt, potassium salt, magnesium salt, calcium salt, or other salts of amino acids, preferably sodium salt.

With exception of glycine, all of the amino acids mentioned in the invention are L-type. The amino acids, oligopeptides and polypeptides can be hydrolysis products (such as tryptone, polypeptone, proteose peptone etc.) of varies kinds of proteins (such as muscular fibrin, hemoglobin, or casein) that are catalyzed by proteinases (such as pepsin, trypsin, or microbial proteinases), acids or alkalis, or the products (such as yeast extract, *lactobacilli* extract) from microbial fermentation substances rich in amino acids, oligopeptides and polypeptides, or amino acids or peptide agents available in markets. It is preferred to use the combination of many amino acids and/or their salts, especially the preferred amino acids or their salts. Alternatively, amino acids and/or their salts are mixed with oligopeptides and polypeptides. It is also preferred to directly use yeast extracts, tryptone, polypeptone or proteose peptone that containing a plenty of amino acids, oligopeptides and polypeptides.

The pharmaceutical composition of this invention may also contains minor kinds of amino acids and/or salts of amino acids, especially the amino acids and/or salts of amino acids selected from the group defined as follows: glutamic acid, aspartic acid, isoleucine, phenylalanine, valine, leucine, proline, threonine. The composition containing only one or two sodium salts of amino acids can also partly realize the object of the invention. Most preferable, the pharmaceutical composition of this invention contains the following amino acids or salts thereof: glutamic acid, aspartic acid, isoleucine, phenylalanine, and proline.

According to the invention, the forms of the composition of the invention can be in the forms of lotion, drops, aerosol spray, suspension, emulsion, creams, tablets, effervescent tablets, suppository, gel, unguentum, micro capsules, sustained release dosage, or any other acceptable vaginal local drug forms. The skilled in the art can mix amino acids, oligopeptides, polypeptides and other effective components with one or more pharmaceutical carriers in a common method to prepare the pharmaceutical formulation described in this invention. The preferred form of the formulation of the invention is viscous gel, and the preferred viscous auxiliary base is Xanthan gum with a concentration ranging from 1.0%-2.5%.

According to different formulations of the pharmaceutical compositions of the invention, the total content of its amino acids can change in a wide range, preferably 30-350 mmol/L and the particular preferred range is 80-200 mmol/L when the composition is in the form of viscous gel, lotion, or emulsion.

According to the invention, the amino acids and/or the physiologically acceptable of amino acids, oligopeptides, polypeptides can be separately used as basic active components to realize the object of the invention. The basic salts of amino acids especially the sodium salts of amino acids are preferable to be comprised in composition to realize the object of this invention.

According to the invention, the composition of the invention can also selectively contain an effective amount of anti-fungal drug to inhibit or kill fungi. The examples of anti-fungal drugs are Terconazole, Tioconazole, Butoconazole, Ketoconazole, Econazole, Miconazole, Cannitracin, Treconazole, Itraconazole and Fluconazole, as well as nucleotide drugs such as 5-Flucytosine.

According to the invention, the composition of the invention can also selectively contain natural pharmaceutical plant products, for example the extracts of Radix *Sophorae Flavescentis*, Monnieri Fructus Cnidii, Herba Hedyotis Diffusae, *Desmodium styracifolium*, and Cortex *Phellodendri*, etc.

The weight/volume content (W/V) mentioned in the context of this application refers to grams of the specified component in 100 milliliter of composition. In liquid compositions, amino acids components can be dissolved or suspended in one kind or more kinds of pharmaceutical carriers. The composition of the invention can be formulated by using the method known to the person skilled in the art.

For example, when the formulation is prepared in the form of a viscous gel, thoroughly mix the effective components such as varies kinds of sodium salts of amino acids with viscous auxiliaries homogeneously. Then add distilled water to the mixture and stir it until the active components are dissolved and viscous auxiliaries swollen into a viscous gel. Then add basic or acidic component, adjust pH value to 4.0-8.0, particularly, to pH 6.5-8.0, sterilize it either by high-pressure or discontinuous sterilization methods.

When suppositories, tablets, effervescent tablets, or capsules are used for the preparation of the composition, amino acids, and/or anti-fungal drugs, and/or plant products can be mixed with other pharmaceutical carriers, granulating, tabletting, or filling in capsules.

The present invention also relates to the use of the above-mentioned amino acids as active components or auxiliary substances in the preparation of the pharmaceutical composition for reducing vaginal acidity, treating an abnormal increase of vaginal acidity and high acidity vaginitis, especially fungal vaginitis associated with high vaginal acidity, and as nutrients of vaginal mucous cells in the preparation of vaginal local composition.

The amino acids and/or the sodium salts of amino acids of this invention can be used to reduce vaginal acidity, treat abnormal increase of vaginal acidity (pH of vaginal secretions<4.0), and high acidity vaginitis especially fungal vaginitis. These substances can also be used as auxiliary substances to make vaginal-using anti-fungal agents, or used as excipient substitutes of starch, lactose and other saccharides to make vaginal using anti-fungi drugs.

Amino acids and/or the physiologically acceptable salts of amino acids are also used as nutrients for preparing therapeutic agents for the vaginal use, or for preparing vaginal sanitation products or other healthcare products.

The experiments showed that the composition of this invention could reduce vaginal acidity. Therefore, it can be used for treating an abnormal increase of vaginal acidity, vaginitis with high vaginal acidity, especially for treating fungal vaginitis associated with high vaginal acidity.

This invention also relates to a method for reducing vaginal acidity, treating an abnormal increase of vaginal acidity, and high acidity vaginitis, especially fungal vaginitis. It includes providing patients with the above-mentioned drugs of this invention at the dosage required for effective therapy, if necessary.

The pharmaceutical composition of this invention is administered locally into the vagina. For example, the composition in the form of effervescent tablets can be placed directly into the vagina. If the composition of this invention is in the form of a solution it can be used to soak intra-vaginal tampons and then place the tampon inside the vagina, or just simply douche the vagina. The composition of this invention in the form of viscous gel can be administered directly into the vagina. The compositions of this invention in the forms of lotion, drop, aerosol spray, tablets, suppository and capsule, can be administered vaginally.

For the composition or method of this invention, the total dosage of amino acids and/or the sodium salts of amino acids can change in a wide range. The preferred amount is 0.01-1.5 g per day. The more preferred dosage is 0.1-1.0 g, administered vaginally once or twice or three times a day.

During the treatment with the composition of this invention, follow the change of clinical symptoms of patient and examine the change of vaginal pH value every day. If possible, a Gram-stained vaginal smear should be examined under microscopy to follow the change of flora. When symptoms disappear or alleviated and the vaginal pH value remains between 4.0 and 4.6, the treatment should be stopped, or the dosage should be reduced.

As for the method of this invention, the patient can be treated with the composition only containing the amino acids and/or the sodium salts of amino acids as active components. Alternatively, the patient can be administered with the composition containing amino acids and/or sodium salts of amino acids, oligopeptides, polypeptides, and basic substances of this invention as active components, or with the composition containing amino acids and/or sodium salts of amino acids, oligopeptides, polypeptides, basic substances, and anti-fungal agents of this invention, or with the anti-fungal agents containing amino acids, oligopeptides and polypeptides of this invention as auxiliary components. Selectively, the composition containing only the amino acids and/or sodium salts of amino acids of this invention can be applied with suitable drugs containing basic substances and/or anti-fungal drugs. The composition of this invention can be administered at the same time or in a sequence with basic substances and/or anti-fungal drugs, with no strict requirement in respect to the administration order.

After application of above-mentioned drugs, the clinical symptoms of the patient can be alleviated quickly, with the vaginal pH value raised above 4.0 and the amount of fungi in the vagina reduced.

For the cases of abnormally high vaginal acidity, the patient can be treated with the medicine of this invention until the symptoms are alleviated and the vaginal pH value remains steadily between 4.0-4.6. When the desired pH is reached, the dosage should be reduced or stopped. For the cases with typical fungal vaginitis, in particular for repeated Candidal vaginitis, the patient can be treated with the composition of this invention containing anti-fungal agents until the symptoms are alleviated and the vaginal pH value remains steadily between 4.0-4.6, then the dosage can be reduced or stopped.

DETAILED DESCRIPTION

This invention will be described in more details by providing the following examples. It should be understood however, that these examples are only for the illustration of this invention, not to impose any restrictions on this invention. All the variants or modifications, which are made based on the principle of this invention, shall be deemed to be included in this invention.

COMPOSITION EXAMPLE

EXAMPLE 1

Composite amino acids of 3.0 g (glutamic acid, aspartic acid, isoleucine, methionine, phenylalanine, tyrosine, valine, leucine, proline of 2.36 mmol each), yeast extract powder of 1.0 g, sodium bicarbonate of 1.0 g and Xanthan gum of 1.6 g are mixed homogeneously, and 100 ml of distilled water is added into the mixture, stirred until all of the components are dissolved, and Xanthan gum swells in the form of homogeneous viscous gum, and then sterilize.

EXAMPLE 2

100 ml of the composition in the following formulation was prepared substantially according to the method as described in Example 1: Tryptone 5.0 g, Xanthan gum 1.6 g, and distilled water q.s.

EXAMPLE 3

100 ml of the composition in the following formulation was prepared substantially according to the method as described in Example 1. Yeast extract powder 3.0 g, sodium lactate 1.5 g, Ketoconazole 2.0 g, Xanthan gum 1.8 g, and distilled water q.s.

EXAMPLE 4

3.0 g of yeast extract powder, 1.0 g of sodium bicarbonate, and 1.6 g of Xanthan gum were mixed homogeneously. Then 100 ml of distilled water was added in the mixture while stirring in order to dissolve the yeast powder and sodium bicarbonate and the Xanthan gum is swollen to homogeneous viscous gum, and then sterilized.

EXAMPLE 5

100 ml of the composition in the following formulation was prepared substantially according to the method as described in Example 1. 0.5 mmol each of the following amino acids: glutamic acid, alanine, aspartic acid, valine, isoleucine, proline, glycine, serine, threonine, lysine, arginine, histidine, methionine, phenylalanine, tyrosine, leucine, cysteine, tryptophane, oxyproline, cystine, ornithine; yeast extract powder 1.0 (W/V); sodium bicarbonate 1.0% (W/V); Xanthan gum 1.6% (W/V); water q.s.; and dispensing agent pH 8.3.

EXAMPLE 6

100 ml of the composition in the following formulation was prepared substantially according to the method as described in Example 1. 1.0 mmol each of the following amino acids: glutamic acid, aspartic acid, isoleucine, proline, methionine, phenylalanine, tyrosine, valine and leucine; 2.0% (W/V) yeast extract powder; 1.5% sodium lactate (W/V); 1.5% (W/V) Xanthan gum; water q.s. The pH value of the composition was adjusted to 6.5.

EXAMPLE 7

0.17 mmol each of the following amino acids: glutamic acid, alanine, aspartic acid, valine, isoleucine, proline, glycine, serine, threonine, lysine, arginine, histidine, methionine, phenylalanine, tyrosine, leucine, cysteine, and tryptophane;

| Sodium bicarbonate | 1.0 g; |
|---|---|
| Ketoconazole | 2.0 g; |
| Xanthan gum | 1.6 g; |
| Distilled water | q.s. |

EXAMPLE 8

100 ml of the composition in the following formulation was prepared substantially according to the method as described in Example 1. 1.5 mmol each of the following amino acids: glutamic acid, glutamine, aspartic acid, asparagine, valine, isoleucine, proline, threonine, phenylalanine, leucine; 0.5 mmol each of the following amino acids: methionine, alanine, glycine, serine, lysine, arginine, histidine, tyrosine, cysteine, and tryptophane;

| Xanthan gum | 1.6 g; |
|---|---|
| Distilled water | q.s. |

EXAMPLE 9

100 ml of the composition in the following formulation was prepared substantially according to the method as described in Example 1. 1.5 mmol each of the following amino acids: glutamic acid, glutamine, aspartic acid, asparagine, valine, isoleucine, proline, threonine, phenylalanine, and leucine; 0.2 mmol each of the following sodium salts of amino acids: sodium salt of methionine, sodium salt of tyrosine, sodium salt of cysteine, sodium salt of alanine, sodium glycinate, sodium salt of serine, sodium salt of lysine, sodium salt of arginine, sodium salt of tryptophane, and sodium salt of histidine.

| Itraconazole | 2 g; |
|---|---|
| Yeast extract powder | 0.8 g; |
| Xanthan gum | 1.6 g; |
| Distilled water | q.s. |

EXAMPLE 10

100 ml of the composition in the following formulation was prepared substantially according to the method as described in Example 1. 1.0 mmol each of the following amino acids: glutamic acid, glutamine, aspartic acid, asparagine, valine, isoleucine, proline, threonine, phenylalanine, and leucine; 0.1 mmol each of the following sodium salts of amino acids: sodium salt of methionined sodium salt of tyrosine, sodium salt of cysteine, sodium salt of alanine, sodium glycinate, sodium salt of serine, sodium salt of lysine, sodium salt of arginine, sodium salt of tryptophane, and sodium salt of histidine. Potassium chloride 0.5 mmol, magnesium chloride 0.16 mmol riboflavin 0.2 ppm, thiamine 0.2 ppm, nicotinic acid 0.2 ppm, calcium pantothenate 0.2 ppm Fluconazole 2 g; Xanthan gum 1.6 g;

EXAMPLE 11

Lotion 100 ml of lotion of this invention was prepared in the following formulation: 1.0 mmol each of the following amino acids: glutamic acid, aspartic acid, valine, isoleucine, proline, threonine, phenylalanine, and leucine; 0.3 mmol each of alanine, glycine, serine, tyrosine, cysteine, tryptophane and methionine.

Water q.s.

EXAMPLE 12

Lotion 100 ml of the lotion of this invention was prepared in the following formulation.

1.0 mmol each of valine, isoleucine, proline, threonine, phenylalanine, and leucine;

1.0 mmol each of sodium glutamate and sodium aspartate;

0.2 mmol each of methionine, alanine, glycine, serine, cysteine, tyrosine, tryptophane, and lysine;

0.1 mmol of adenine, guanine, uracil, and cytosine;

200 mg of Vitamin C;

100 ml of extract of natural herbs: 30 g each of Radix Sophorae Flavescentis☐Monnieri Fructus Cnidii and Herba Hedyotis Diffusae, and sink the mixture in 250 ml of water at a temperature from 90-100° C. for 40 minutes, and then filtrate the residue and obtain the extract of the herb.

EXAMPLE 13

100 ml of lotion of this invention was prepared in the following formulation.

1.0 mmol each of isoleucine, valine, proline, threonine;

sodium salt of leucine, sodium glutamatedsodium aspartate, sodium salt of phenylalanine;

150 mg of yeast extract powder;

1.5 g of Clotrimazole

Water q.s.

EXAMPLE 14

Composition in Capsules the materials of amino acids are mixed homogeneously in the following formulation, and then packed into capsules, with each capsule containing a total weight of 0.5 g of amino acids sodium salt of amino acids, and 50000 units of mikostatin:

1.0 mmol each of valine, isoleucine, proline, threonine, phenylalanine, leucine, glutamic acid, and aspartic acid;

150 mg of yeast extract powder;

and 120000 units of mikostatin (Note: the total weight of the above-mentioned amino acids and oligopeptide, etc. is about 1200 mg)

EXAMPLE 15

Composition in Suppository

By using glycerin and gelatin as substrate (the proportion of water, gelatin and glycerin is water: gelatin: glycerin=10: 20:70), the composition in the form of suppository in the following formulation was prepared according to the method known to the skilled in the art, with each suppository containing a total amount of 0.5 g of amino acids/sodium salt thereof and 0.1 g of miconazole.

1.0 mmol each of valine, isoleucine, proline, threonine, phenylalanine, leucine, sodium glutamate, and sodium aspartate;

150 mg of yeast extract powder;

0.24 g of miconazole

Substrate for suppository.

EXAMPLE 16

Composition in the Form of Unguentum

By using glycerin and gelatin as the substrates (10-30% of glycerin and 1-3% of gelatin), the composition in the following formulation in the form of unguentum was prepared according to the method known to the skilled in the art:

1.0 mmol each of valine, isoleucine, proline, threonine, phenylalanine, leucine, glutamic acid, and aspartic acid;

150 mg of yeast extract powder;

12 g of unguentum substrate.

EXAMPLE 17

Composition in the Form of Tablets by using Xanthan gum or gelatin as adhesive, and sodium bicarbonate as disintegration agent, magnesium stearate as lubricant, the composition in the form of effervesce tablets in the following formulation was prepared according to the method known to the skilled in the art. Each tablet contains a total weight of 0.5 g of amino acids, oligopeptides and polypeptides as well as 0.1 g of Ketoconazole. Note that no sugar or starch is added;

1.0 mmol each of valine, isoleucine, proline, threonine, phenylalanine, leucine, glutamic acid, and aspartic acid;

150 mg of yeast extract powder;

0.24 g of Ketoconazole.

EXAMPLE 18

Composition in Capsules

The amino acids are used in the following formulation, and packed into the capsules after being mixed homogeneously, with each capsule containing 0.5 g of sodium glutamate and 50000 units of mikostatin:

| | |
|---|---|
| Sodium glutamate | 500 g |
| mikostatin | 50,000,000 units |

EXAMPLE 19

Composition in Suppository

By using glycerin and gelatin as substrate (the proportion of water to gelatin to glycerin is 10:20:70), composition in the form of suppository in the following formulation was prepared according to the method known to the skilled in the art, with each suppository containing sodium glutamate and sodium aspartate of 0.25 g each and miconazole of 0.1 g:

| | |
|---|---|
| Sodium glutamate | 250 g |
| Sodium aspartate | 250 g |
| Miconazole | 100 g |
| Suppository substrate | |

EXAMPLE 20

100 ml of the composition in the following formulation was prepared substantially according to the method as described in Example 1.

1.0 mmol each of the following sodium salt of amino acids: sodium glutamate, sodium aspartate, sodiuim of isoleucine, sodium salt of phenylalanine, sodium salt of valine, sodium salt of leucine, sodium salt of proline, and sodium salt of threonine;

0.1 mmol each of the following sodium salts of amino acids: sodium salt of methionine, sodium salt of tyrosine, sodium salt of cysteine, sodium salt of alanine, sodium glycinate, sodium salt of serine, sodium salt of lysine, sodium salt of arginine, sodium salt of tryptophane, and sodium salt of histidine.

Potassium chloride 0.5 mmol, magnesium chloride 0.16 mmol Adenine 0.2 mmol, guanine 0.2 mmol, uracil 0.2 mmol, and cytosine 0.1 mmol;

riboflavin 0.2 ppm, thiamine 0.2 ppm, nicotinic acid 0.2 ppm, calcium pantothenate 0.2 ppm Xanthan gum 1.6 g;

Distilled water q.s.

The effectiveness of the composition or method of this invention is illustrated by the following experimental examples:

EXAMPLE 21

100 ml of the composition in the following formulation was prepared: 1.75 mmol of each sodium salts of the following amino acids: glutamic acid, aspartic acid, isoleucine, phenylalanine, valine, leucine, proline threonine;

1.0 g Fluconazole;

1.0 g Xanthan gum;

The above ingredients are mixed homogeneously, then added 100 ml distilled water, stirred, until all of the components are dissolved. Adjust pH value to 6.5-7.5, sterilize.

EXAMPLE 22

100 ml of the composition in the following formulation was prepared substantially according to the method as described in Example 1.

4.375 mmol of each sodium salts of the following amino acids: glutamic acid, aspartic acid, isoleucine, phenylalanine, valine, leucine, proline threonine;

2.0 g Ketoconazole;

2.5 g Xanthan gum;

100 ml distilled water.

Adjust pH value to 6.5-7.5

EXAMPLE 23

100 ml of the composition in the following formulation was prepared substantially according to the method as described in Example 1.

0.5 mmol each of the following amino acids: glutamic acid, alanine, aspartic acid, valine, isoleucine, proline, glycine, serine, threonine, lysine, arginine, histidine, methionine, phenylalanine, tyrosine, leucine, cysteine, tryptophane, oxyproline, cystine, ornithine;

1.0 g Sodium bicarbonate;

1.6 g Xanthan gum;

100 ml distilled water;

Adjust pH to 7.0

EXAMPLE 24

100 ml of the composition in the following formulation was prepared according to the method as described in Example 1.

1.6 mmol each of the following amino acids: glutamic acid, aspartic acid, isoleucine, proline, phenylalanine;

1.0 g Tioconazole;

1.5 g Xanthan gum;

100 ml distilled water

The pH value of the composition is adjusted to 6.5 to 7.5

EXAMPLE 25

100 ml of the composition in the following formulation was prepared according to the method as described in Example 1.

4.0 mmol of each sodium salts of the following amino acids: glutamic acid, aspartic acid, isoleucine, proline, phenylalanine;

1.5 g Ketoconazole;

1.5 g Xanthan gum;

100 ml distilled water

The pH is adjusted to 6.5 to 7.5

EXAMPLE 26

100 ml of the composition in the following formulation was prepared substantially according to the method as described in Example 1.

1.5 mmol of each sodium salts of the following amino acids: glutamic acid, glutamine, aspartic acid, asparagine, valine, isoleucine, proline, threonine, phenylalanine, leucine; 0.5 mmol each of the following amino acids: methionine, alanine, glycine, serine, lysine, arginine, histidine, tyrosine, cysteine, and tryptophane;

0.3 g Fluconazole 1.6 g Xanthan gum;

100 ml Distilled water.

Adjust pH value to 6.5 to 7.5

EXAMPLE 27

Lotion 100 ml of lotion of this invention was prepared in the following formulation:

1.0 mmol of each sodium salts of the following amino acids: glutamic acid, aspartic acid, valine, isoleucine, proline, threonine, phenylalanine, and leucine;

0.3 mmol each of alanine, glycine, serine, tyrosine, cysteine, tryptophane and methionine;

1.0 Fluconazole;

100 ml distilled water

EXAMPLE 28

Lotion 100 ml of the lotion of this invention was prepared in the following formulation.

2.0 mmol each of the following amino acids: glutamic acid, aspartic acid, isoleucine, proline, phenylalanine;

1.0 Fluconazole;

100 ml of extract of natural herbs: 30 g each of Radix *Sophorae Flavescentis*☐Monnieri Fructus Cnidii and Herba Hedyotis Diffusae, and sink the mixture in 250 ml of water at a temperature from 90-100° C. for 40 minutes, and then filtrate the residue and obtain the extract of the herb.

The effectiveness of the composition or method of this invention is illustrated by the following experimental examples:

Typical Case Report

EXPERIMENTAL EXAMPLE 1

Case 1, female, 32 years old, suffering from vaginal pruritus, accompanying pains for two years, severe before menstruation and alleviated after menstruation, diagnosed with repeated fungal vaginitis. After treatment with anti-fungal drugs and washing the vagina, her illness improved, but she suffered from the illness again after the medication was ceased. The inventor performed an inspection on her vaginal secretion and the test result of its pH value was less than 3.8, the vaginal smear indicated fungal spores, so the patient was diagnosed with "high-acidity vaginitis and accompanying fungal vaginitis". 3 ml of the composition of this invention (shown in Example 1) was administered twice a day. After application of the drug for one day, the symptoms were alleviated substantially and the secretion quantity was reduced. After application of the drug for three days, pruritus vulvae disappeared and test results of vaginal secretion revealed pH 4.4, and the smear dyeing indicated that there were no fungal spores. The patient did not take the medication any more, and the pH value in the vagina was less than 4.0, again, two weeks after menstruation, with the symptoms substantially alleviated than prior to treatment. Therefore 1 ml of the composition of this invention was used again, twice a day until the symptoms disappear. Such treatment continued for three weeks and afterwards the patient never suffered from the illness.

EXPERIMENTAL EXAMPLE 2

Case 2, female, 30 years old, suffered from pruritus vulvae and leukorrhagia accompanyed with dyspareunia for more than one year. The patient had pruritus vulvae and pains with a feeling of burning, especially before menstruation, feeling anxious accompanying leukorrhagia and dyspareunia. This patient was diagnosed with fungal vaginitis. Effervescent tablets containing miskostatin and ketoconazole Cream was administered locally into the vagina with fluconazole taken orally. During the use of the drugs the symptoms were alleviated substantially, but after ceasing administration of the drugs, or after menstruation, the illness returned slowly and became more severe. The inventor performed inspection on her vaginal secretions which revealed a pH value of less than 3.8, the vaginal smear dyeing showed no fungal spores and fungal filaments, and a diagnosis of "high-acidity vaginitis" was made. The patient was treated with the composition of this invention (as shown in Example 2) with 4 ml of the composition administered twice a day. After application of the drug for one day, pruritus vulvae was alleviated substantially and the leukorrhagia was reduced, with analysis of vaginal secretions showing a pH value of 4.0. After application of the drug for three days, vaginal secretion was pH 4.4. Such treatment continued with reduced quantity, and after two months, the illness was cured completely, and the patient never suffered from the illness again.

EXPERIMENTAL EXAMPLE 3

Case 3, female, 28 years old, suffered from pruritis vulvae, pains with a feeling of burning and leukorrhagia accompanyed with coagulate like bean curd for more than half year. The patient was diagnosed as "fungal vaginitis." The treatment with anit-fungal drags may control the symptoms, but the administration can not be ceased. The inventor performed an inspection, the pH of her vaginal secretions is less than 3.8, there are many fungal filaments in the vaginal secretions. The patient was administrated with the composition of this invention (as shown in example 3), with 3 ml twice a day. Two days later, pruritis vulvae and pain were alleviated significantly, the lenkorrhagia was reduced, the coagulate like bean curd was disappeared. Investigations indicated that the vaginal acidity was reduced and pH value of the secretion was 4.0, and there was no fungi. The drug was applied until the pH value of vaginal secretion was 4.4.

EXPERIMENTAL EXAMPLE 4

Case 4, female, 38 years old, suffered from repeated pruritis vulvae for more than one year, severe before menstruation and alleviated after menstruation. The inventor investigated the vaginal secretion and found its pH value is 3.8, the smear dyeing found no fungal spores, and a diagnosis of "high-acidity in vagina accompanying fungal infection" was made. The composition of this invention (shown in Example 8) was administered twice a day with 3 ml being administered each time. After application of the drug for one day, the symptoms were alleviated substantially and the vaginal secretion quantity was reduced. After application of the drug for three days, pruritis vulvae disappeared and investigations revealed that the pH of vaginal secretion was pH 4.4, the smear dyeing indicated no fungal spores. The patient ceased taking the drug.

EXPERIMENTAL EXAMPLE 5

Case 5, female, 27 years old, suffered from repeated pains with a feeling of burning in her vulvae, accompanied with coagulate like bean curds for half a year. The inventor examined this lady and found that the pH of her vaginal secretions is<3.8, there was no fungal spores and filaments in the secretion. She was treated with the composition of this invention (shown in Example 11), twice a day with 10 ml administered at each time. After application of the drug for three days, the pruritis with other symptoms were significantly reduced. Also, leukorrhagia was reduced, without coagulate residues like bean curd, the pH value of the vaginal swab was 4.0 and no fungi was found. This treatment outcome resulted in the dosage being reduced to once a day. After two days, the vaginal swab was examined, pH=4.4, the medication was ceased.

EXPERIMENTAL EXAMPLE 6

Case 6, female, 35 years old, suffering from abnormal vaginal discharges and vulvae discomfort for half year. The inventor examined her vaginal secretion under microscopy and found fungal spores. Vaginal pH was lower than 3.8. So the patient was diagnosed as "high-acidity vaginitis and fungal vaginitis". 3 ml of the composition in Composition Example 21 was administered twice a day. One day later after application of the drug the symptoms were alleviated substantially and the secretion reduced. Three days later after the treatment, pruritus vulvae disappeared and her vaginal pH was 4.4. Examining her vaginal smear again no fungal spores were found. Then the dosage reduced to 1 ml once a day, for two more weeks. The patient didn't suffer from the illness anymore in the following three months.

EXPERIMENTAL EXAMPLE 7

Case 7, female, 40 years old, suffered from pruritus vulvae and leukorrhagia for more than one year. Had been diagnosed and treated as Candidal vaginitis. However, it relapsed repeatedly. The inventor examined her vaginal secretions which revealed a pH value of less than 3.8, the Gram-stained vaginal smear showed fungal spores as well as fungal filaments. Diagnosed as "fungal vaginitis associated with high vaginal acidity", the patient was treated with the composition in Composition Example 25 of this invention, 4 ml of the composition administered once a day. After application of the drug for one day, pruritus vulvae was alleviated significantly and the leukorrhagia was reduced. Vaginal pH increased to 4.0. After using the drug for three more days, vaginal secretion pH was 4.4. The treatment was continued by reduced dosage for two weeks. The illness was cured and the patient didn't suffer from the illness again in several months afterwards.

Experiment in Vitro:
The influence of amino acids on the production of acids and the effect of anti-fungi drug on the growth of fungi.

Objective

To study the effect of a combination of amino acids on the production of acids by *lactobacilli* and to study the effect of Fluconazole on the growth of *Candida albicans* strain.

Materials and Methods

1. Materials:
   Broths: Four sterilized broths were prepared separately according to following formula:
   A. Sucrose 0.25%, yeast extract powder 0.15%, glutamic acid 0.4%, aspartic acid 0.4%, isoleucine 0.4%, proline 0.4%, phenylalanine 0.4%, Fluconazole, 0.005%, distilled water, pH adjusted to 6.5
   B. Sucrose 0.25%, yeast extract powder 0.15%, glutamic acid 0.08%, aspartic acid 0.08%, isoleucine 0.08%, proline 0.08%, phenylalanine 0.08%, Fluconazole, 0.005%, distilled water, pH adjusted to 6.5
   C. Control-A broth: Sucrose 0.25%, yeast extract powder 0.15%, glutamic acid 0.4%, aspartic acid 0.4%, isoleucine 0.4%, proline 0.4%, phenylalanine 0.4%, distilled water, pH adjusted to 6.5
   D. Control-B broth: Sucrose 0.25%, yeast extract powder 0.15%, glutamic acid 0.08%, aspartic acid 0.08%, isoleucine 0.08%, proline 0.08%, phenylalanine 0.08%, distilled water, pH adjusted to 6.5
   *Lactobacillus* suspensions: Two *lactobacillus* suspensions were prepared separately from each of the clinical isolated *L. acidophilus* and *L. crispatus* strains.
   *Candida* suspension: One *Candida* suspension was prepared from a clinically isolated *Candida albicans* strain.

2. Methods:
   Grouping: two groups of tubes were divided and each group had four tubes, two experimental tubes and two control tubes. Group A contained 3 ml of A-broth and Group B contained 3 ml of B-broth. Control tube contained broth as the same as it's experimental tube except without Fluconazole.

The turbidity value of two *lactobacillus* suspensions and *C. albicans* suspension were tested by Turbidimeter and adjusted to 0.3. 50 ul of each prepared *lactobacillus* suspension and 10 ul of *C. albicans* suspension was separately added into tubes according to Table 1.

TABLE 1

| | The groups of experiment | |
|---|---|---|
| Tubes | Group-A | Group-B |
| Tube 1 | L. acidophilus | L. acidophilus |
| | C. albicans | C. albicans |
| Tube 2 | L. crispatus | L. crispatus |
| | C. albicans | C. albicans |
| Control 1 | L. acidophilus | L. acidophilus |
| | C. albicans | C. albicans |
| Control 2 | L. crispatus | L. crispatus |
| | C. albicans | C. albicans |

All of these tubes were put into a candle jar as soon as the *lactobacillus* suspensions and *Candida* suspension were added, and then incubated at 37° C. for 48 hours.

pH values of the cultured broths were tested at 24 hours and 48 hours. And the Gram-stained smears of cultured broths were examined with microscopy.

Results: The results are shown in Table 2.

*Lactobacilli* grew in all tubes and Gram-stained smears of the cultured broths showed *lactobacilli*-like Gram-positive bacilli. Yeast-like organisms were found in all of the control tubes but not in any of the experiment tubes. Testing the pH values of all cultured broths showed the low pH values in Group-B and Control-B at 48 hours, which were significantly lower than those of Group-A and Control-A. It suggested that more acids were produced in Group B and Control-B after 48 hours incubation.

In experiment groups there were no yeast-like organisms being found, while in control tubes there were yeast-like organisms. It showed that growth of *Candida albicans* in experiment tubes were inhibited by Fluconazole.

TABLE 2

The effect of a combination of amino acids on the production of acid by lactobacilli and the effect of Fluconazole on the growth of *Candida albicans* strain

| | 24 hours | | 48 hours | |
|---|---|---|---|---|
| | pH | Smear | pH | Smear |
| Group-A | | | | |
| L. acidophilus | 5.4 | GPB* | 5.2 | GPB |
| L. crispatus | 5.6 | GRB | 5.4 | GPB |
| Group-B | | | | |
| L. acidophilus | 5.1 | GPB | 4.6 | GPB |
| L. crispatus | 5.4 | GPB | 4.8 | GPB |
| Control-A | | | | |
| L. acidophilus | 5.4 | GPB, C** | 5.3 | GPB, C |
| L. crispatus | 5.6 | GRB, C | 5.6 | GPB, C |

TABLE 2-continued

The effect of a combination of amino acids on the
production of acid by lactobacilli and the effect of
Fluconazole on the growth of *Candida albicans* strain

|  | 24 hours | | 48 hours | |
| --- | --- | --- | --- | --- |
|  | pH | Smear | pH | Smear |
| Control-B |  |  |  |  |
| L. acidophilus | 5.4 | GPB, C | 4.8 | GPB, C |
| L. crispatus | 5.4 | GPB, C | 4.8 | GPB, C |

*GPB: Gram-Positive *bacilli*
**C: *Candida albicans*

Discussion:

The results of this experiment suggested there was more production of acids in Group-B and Control-B after 48 hours incubation. As there was much less amount of the combination of five amino acids in Group-B and Control-B than in Group-A and Control-A, it suggested strongly that the combination of these five amino acids could reduce the production of acids by *lactobacillus* strains.

C. *Candida albicans* grew in Control tubes but not in Experiment tubes. This showed that the combination use of Fluconazole and amino acids was able to reduce the production of acids and inhibit the growth of *Candida* at the same time. In Control-A tubes though the production of acids were reduced by a combination of five amino acids, the *Candida albicans* still grew. The combination of amino acids itself was not able to inhibit or kill the *C. albicans*. Thus the combination use of anti-fungi drug and amino acids may be a desirable choice for the treatment of fungi vaginitis with high vagina acidity.

The invention claimed is:

1. A vaginal use composition for treating a patient suffering from abnormally high acidity in the vagina, wherein the vaginal pH value is lower than 4.0, the said composition comprising:

a. an effective amount of an amino acid mixture (or the like) comprising: glutamic acid, aspartic acid, isoleucine, phenylalanine and proline and/or physiologically acceptable salts thereof b. An effective amount of anti-fungi drugs;

c. A sufficient amount of pharmaceutically acceptable acid or alkali, which results in a pH of the composition from 4.0-8.0;

d. One or more pharmaceutical carriers.

2. The composition according to claim 1, wherein the said composition further comprising one or more of the following amino acids and/or physiologically acceptable salts thereof: valine, leucine, threonine.

3. The composition according to claim 2, wherein the said composition further comprising one or more of the following amino acids and/or physiologically acceptable salts thereof: methionine, tyrosine, cysteine, alanine, glycine, serine, lysine, glutamine, asparagine, arginine, tryptophane and histidine.

4. The composition according to claim 1, wherein the said composition comprising: sodium salt of glutamic acid, sodium salt of aspartic acid, sodium salts of isoleucine, sodium salt of phenylalanine, sodium salt of proline.

5. The composition according to any one of claims 1 to 4, wherein the said physiologically acceptable salts of amino acids are sodium salt, potassium salt, calcium salt, or magnesium salt of amino acids.

6. The composition according to any one of claims 1 to 4, wherein the said composition is in the form of viscous gels, lotion, tablets, effervescent tablets, suppositories, emulsion, ointments or micro-capsules.

7. The composition according to claim 6, wherein when the said composition is in the form of viscous gel, lotion or emulsion, the total amount of amino acids and the physiologically acceptable salts thereof is in the range of 30-350 mmol/L.

8. The composition according to claim 6, wherein the said viscous base is Xanthan gum.

9. The composition according to claim 7, wherein the total amount of amino acids and the physiologically acceptable salts thereof is in the range of 80-200 mmol/L.

10. The composition according to claim 1, wherein the said anti-fungi drug is selected from the following group: Fluconazole, Terconazole, Tioconazole, Butoconazole, Ketoconazole, Itraconazole, Econazole, Miconazole, Cannitracin.

11. The composition according to claim 10, wherein the said anti-fungi drug is selected from the following group: Fluconazole, Terconazole, Tioconazole.

* * * * *